(12) United States Patent
Sapala et al.

(10) Patent No.: US 6,758,219 B2
(45) Date of Patent: Jul. 6, 2004

(54) SAPALA-WOOD℠ MICROPOUCH

(75) Inventors: James A. Sapala, Ann Arbor, MI (US); Michael H. Wood, Bloomfield, MI (US)

(73) Assignee: MSO Medical, Bannockburn, IL (US)

(*) Notice: Subject to any disclaimer, the term of this patent is extended or adjusted under 35 U.S.C. 154(b) by 119 days.

(21) Appl. No.: 10/237,327

(22) Filed: Sep. 6, 2002

(65) Prior Publication Data

US 2004/0045562 A1 Mar. 11, 2004

(51) Int. Cl.[7] ............................................. A61B 19/00
(52) U.S. Cl. ..................................... 128/898; 606/151
(58) Field of Search ........................................ 128/898

(56) References Cited

U.S. PATENT DOCUMENTS

| 4,315,509 A | 2/1982 | Smit |
| 5,226,429 A | 7/1993 | Kuzmak |

OTHER PUBLICATIONS

Fox SR, Oh KH, Fox K. Vertical banded gastroplasty and distal bypass as primary procedures: a comparison. Obes Surg 1996; 6: 421–425.
Livingston EH. Obesity and its Surgical management. The American Journal of Surgery 2002; 184: 103–113.
MacLean LD, Rhode BM, Nohr C, et al. Stomal ulcer after gastric bypass. J Am Coll Surg 1997; 185: 1–7.
Mason EE. Development of operations for obesity. Surgical treatment of obesity. Major problems in clinical surgery, Ebert PA, ed. vol. XXVI. Philadelphia: W.B. Saunders, 1981:1–60.
Printen KJ, Scott D, Mason EE. Stomal ulcers after gastric bypass. arch Surg 1980; 115: 525–527.
Sapala MA, Sapala JA, and Hurtado M. Technique for the anatomic placement of the Angelchik anti–reflux prosthesis. Surg Gynecol Obstet 1984; 158: 178–180.
Sapala JA, Brown TE, Sapala MA. Anatomic closure of midline incision of the upper part of the abdomen. Surg Gynecol Obstet 1986; 153: 179–180.
Sapala MA, Sapala JA, Resto Soto AD, et al. Gastric bypass in patients weighing more than 500 pounds: Technical innovations for the "ultra–obese." Obes Surg 1992; 2:253–261.
Sapala JA, Sapala MA, and Wood MH. Nealry total gastric bypass for morbid obesity: a preliminary report in 173 patients. Obes Surg 1996; 6: 126–129.
Sapala JA, Wood MH, Sapala MA, et al. Stapler division of the omentum and the small bowel mesentery in morbidly obese patients undergoing gastric bypass surgery. Obes Surg 1997; 7: 207–210.
Sapala JA, Wood MH, Sapala MA, and Flake TH. Marginal ulcer after gastric bypass a prospective 3–Year study of 173 patients. Obes Surg 1998; 8: 505–516.
Sapala JA et al. Micropouch gasteric bypass. Obes Surg 2001; 11: 410.

*Primary Examiner*—Corrine McDermott
*Assistant Examiner*—William H. Matthews
(74) *Attorney, Agent, or Firm*—Howrey Simon Arnold & White, LLP

(57) ABSTRACT

The present invention is an improved gastric bypass, a surgical method to treat clinically significant obesity, in which the likelihood of post-surgical complications is reduced.

4 Claims, 1 Drawing Sheet

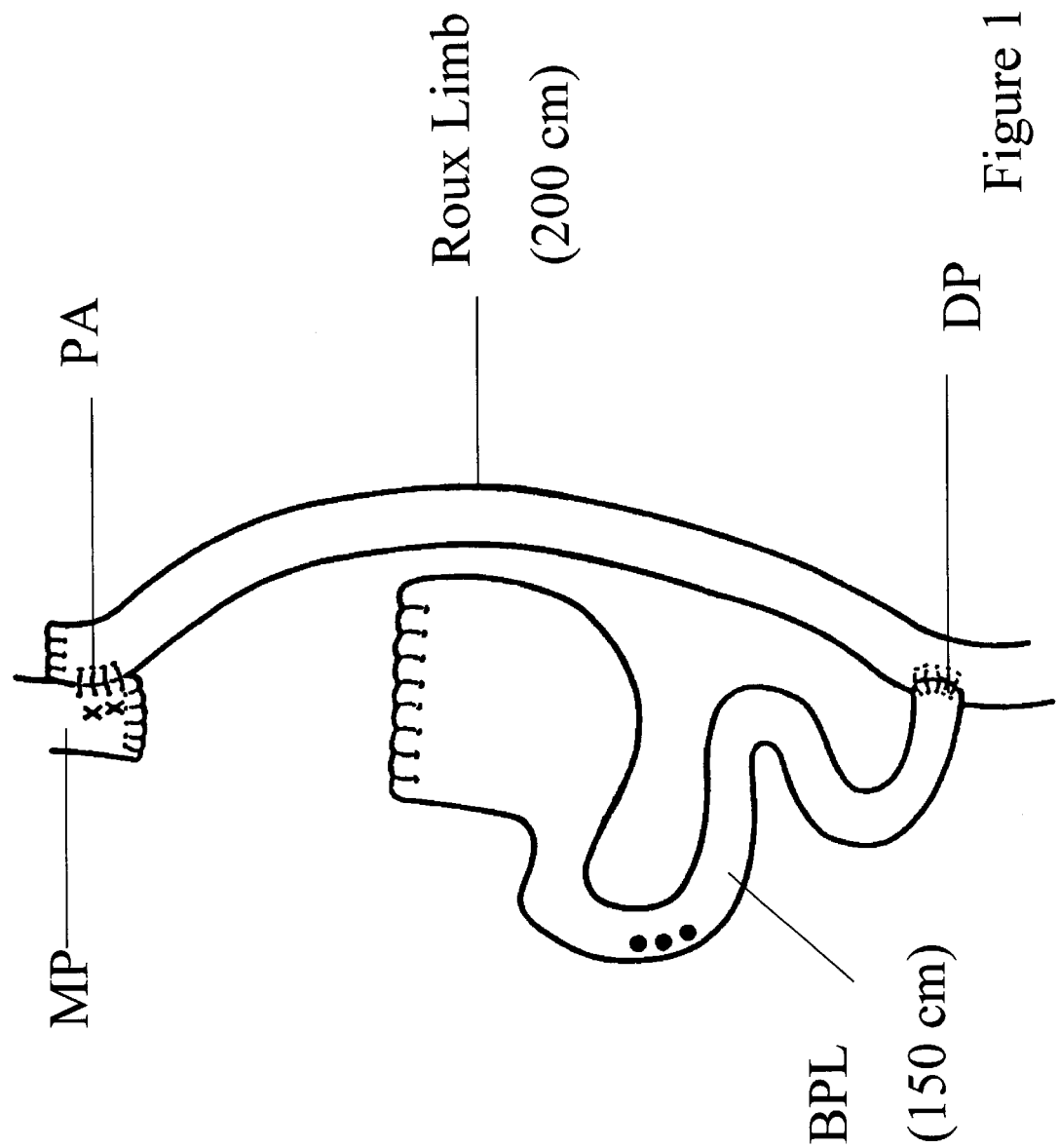

SAPALA-WOOD℠ MICROPOUCH

FIELD OF THE INVENTION

The present invention relates to an improved surgical method for gastric bypass for treating obesity.

BACKGROUND OF THE INVENTION

Obesity is increasing in epidemic proportions world-wide. Even mild degrees of obesity have adverse health effects and are associated with diminished longevity. For this reason aggressive dietary intervention is recommended. Patients with body mass indices exceeding 40 have medically significant obesity in which the risk of serious health consequences is substantial, with concomitant significant reductions in life expectancy. For these patients, sustained weight loss rarely occurs with dietary intervention. For the appropriately selected patients, surgery, (bariatric surgery), is associated with sustained weight loss for seriously obese patients who uniformly fail nonsurgical treatment. Various operations have been proposed for the treatment of obesity, many of which proved to have serious complications precluding their efficacy. A National Institutes of Health Consensus Panel reviewed the indications and types of operations, concluding that the banded gastroplasty and gastric bypass were acceptable operations for treating seriously obese patients. Following weight loss there is a high cure rate for diabetes and sleep apnea, with significant improvement in other complications of obesity such as hypertension and osteoarthritis (Livingston, *Amer J Surg*, 2002; 292: 60–61).

Open gastric bypass surgery is a surgical procedure aiming to decrease the size of patient's stomach. It includes transecting the stomach and constructing a pouch from a portion of the stomach as well as connecting the pouch to the intestine (anastomosis) so that the digested food from the pouch moves into the small bowel (Sapala et al., *Obes Surg* 1998; 8: 253–261). Although, gastric bypass surgery helps patients to lose weight and relieves life-threatening diseases associated with extreme obesity, there are several major post-surgery complications which may require additional treatment. These complications include pouch enlargement, marginal ulceration and staple line separation (dehiscence) (Sapala et al., *Obes Surg* 1998; 8: 505–516).

Marginal ulcer (MU) is defined as a gastric ulcer of the jejunal mucosa near the site of a gastrojejunostomy (Dorland's *Medical Dictionary* 1994). The incidence of marginal ulcers after Roux-en-Y gastric bypass varies between 1% and 16% (MacLean et al., *J Am Coll Surg* 1997; 185: 1–7; Printen et al, *Arch Surg* 1980; 115: 525–527). Known factors that contribute to the development of MU are disruption of the gastric reservoir staple line, large gastric pouches, mucosal ischemia, and the presence of foreign bodies such as silk, Marlex™, or Gore-Tex™ (Sapala et al., *Obes Surg* 1998; 8: 505–516).

One of the most common causes of MU is the presence of a large gastric pouch (MacLean et aL, *J Am Coll Surg* 1997; 185: 1–7; Printen et al., *Arch Surg* 1980; 115: 525–527). In the large gastric bypass pouches (>50 cc), oxynic cell concentration on both sides of the partitioned staple line may lead to MU. The parietal cell mass in the pouch may be large enough in the absence of vagotomy to produce acid-pepsin digestion of the jejunal mucosa. By the contrast, the size of the parietal cell mass below the gastric partition may be reduced, which results in loss of duodenal acidification and secretin stimulation. Unopposed G-cell production of gastrin leads to increased hydrochloric acid secretion by the gastric reservoir parietal cells and subsequent MU (Mason in *Major Problems in Clinical Surgery*, 1981: 1–60, Ebert P A, ed. Vol. XXVI, Philadelphia: W. B. Saunders).

In gastric bypass procedures with vagally innervated pouches <50 cc in volume, the critical size of the parietal cell mass necessary to produce MU is not known. Moreover, gastric pouches initially measured at 50 cc may become greatly enlarged over time. Chronic overeating in the presence of an unrestricted elastic fundus can change the original size of the pouch significantly. Therefore, many surgeons prefer to isolate the fundus from the pouch by limiting the pouch to the lesser curvature (MacLean et al., *J Am Coll Surg* 1997; 185: 1–7; Fox S R et al., *Obes Surg* 1996; 6: 421–425; Sapala J A et al., *Obes Surg* 1997; 7: 207–210). Unfortunately, oxynic cell mass is concentrated along the proximal magenstrasse, which explains why MU in lesser-curvature pouches appears to be more common than in greater-curvature pouches (Sapala et al., *Surg Gynecol Obstet* 1984; 158: 178–180).

Given the benefits of gastric bypass surgery to morbidly obese patients, there is need in the field for improvement of the procedure in order to minimize complications specified above. The present invention is an improved gastric bypass method that helps to avoid common post-operational complications associated with classic gastric bypass.

SUMMARY OF THE INVENTION

The present invention relates to an improved method for gastric bypass surgery which aids in reducing the incidence of common side effects associated with other bariatric surgical methods. Briefly, the method comprises incising the abdominal cavity of the patient, mobilizing the gastrocolic omentum from the watershed to the angle of His and incising the left phrenoesophageal ligament to expose the junction of the longitudinal muscle fibers of the esophagus with the serosa of the cardia. Once the junction is identified, a window is opened along the lesser curvature of the stomach through the gastrohepatic ligament just proximal to the coronary vein. The proximal jejunum is then divided and the Roux-en-Y limb of jejunum (Sapala et al., *Obes Surg* 1998; 8: 505–516) is delivered through an opening in the transverse mesocolon. The proximal end of the stomach is then transected at the junction of the cardia and the fundus. The cardia of the stomach is then used to construct a micropouch. A retrocolic side-to-side Roux-en-Y cardiojejunostomy along greater curvature of the stomach is then performed. The proximal fundus of the cardia is then incorporated into the stoma of the anastomosis which is about 10 mm to about 12 mm in diameter. The gastrotomy and jejunotomy incisions are then closed with interrupted serosal sutures without inverting the staple line at the apex of the micropouch. Fibrin glue (e.g., Hemaseel™) is then applied over the closure. The biliopancreatic limb is then connected to a common conduit consisting of both distal jejunum and the entire ileum. The connection is a stapled anastomosis with a 2.5-cm lumen. The anastomosis is sutured and no glue is applied over the closure.

BRIEF DESCRIPTION OF THE DRAWINGS

FIG. 1 is a schematic diagram of the completed micropouch gastric bypass (Sapala-Wood bypass). MP—micropouch, PA—proximal anastomosis, DP—distal anastomosis, BPL—biliopancreatic limb, Roux Limb—Roux-en-Y limb.

DETAILED DESCRIPTION OF THE INVENTION

Although efficient in treating obesity and diseases associated with it, the classic gastric bypass procedures often result in several characteristic complications, each of which may require additional treatment. Among these complications is the dilation of the gastric pouch constructed during the bypass procedure. It has been noted that even when a 30 cc gastric pouch was used in the standard Roux-en-Y bypass, as many as one third of the patients developed significant dilation of the micropouch.

In an attempt to avoid this problem, the surgeons attempted to limit the pouch (micropouch) to the cardia of the stomach because it was found that it is the elastic fundus incorporated into the pouch that primarily dilates after surgery. The use of the cardia in constructing the micropouch has the advantage that it is relatively inelastic and thus it not prone to dilation and it contains no acid producing cells which could give rise to marginal ulceration. Despite the attempts to limit the pouch to cardia, several patients even dilated the micropouch after surgery.

Upon reexamination, it was determined that a portion of the fundus was hiding under the left pheno-esophageal ligament. Therefore, this ligament must be divided in order to place the staple gun used in constructing the micropouch across the cardia, excluding all fundal tissue from the micropouch.

The present invention provides a technique by which to exclude the gastric fundus from the micropouch, thereby minimizing or eliminating the complications associated with inclusion of the gastric fundus in the micropouch.

The method of the present invention allows the identification of the true junction between the esophagus and the stomach and therefore allows the construction of a micropouch which excludes the fundus and as a result is limited to the cardia of the stomach.

The basic approach to accomplish this goal involves dissecting the left phrenoesophageal ligament off of the cardia of stomach thereby allowing identification of the true junction between the esophagus and the stomach. The identification of this true junction allows construction of a micropouch free of excess fundal tissue.

In certain embodiment of the present invention, the anastomosis between the micropouch and the intestine is sealed with a fibrin glue (e.g., Hemaseel glue [Hemaecure Corp.]). In earlier methods of gastric bypass surgery, the apex of the micropouch was connected with an inverted staple line. However, in one embodiment of the present invention an inverted staple line is not used (uninverted staple line). The elimination of the inverted staple line and the use of the fibrin glue allow the fast and efficient empting of the esophageal and micropouch contents into the intestine. The example set out below is presented by way of illustration and is not entitled to limit the invention as set out in the appended claims. Certain modifications to the method will be apparent to those of ordinary skill in the art and are encompassed by the appended claims.

EXAMPLE 1

Improved Sapala-Wood Micropouch[SM]

In the micropouch gastric bypass operation of the present invention, a midline incision is made from the xiphostemum to the umbilicus. A dissection is carried down through the subcutaneous tissues to the level of the linea alba. A window is then opened in the peritoneum lateral to the midline incision and the abdominal cavity is entered. This allows placement of the self-retaining retractor system which gives access to the left upper quadrangle of the abdomen. The gastrocolic omentum is then taken down from the watershed to the gastroesophageal junction, completely mobilizing the gastric fundus and obliterating the angle of His. Preferably most of this mobilization is accomplished utilizing a harmonic scalpel (Ethicon Corp.).

On occasion, large short gastric vessels are individually ligated using fine silk sutures. The left phrenoesophageal ligament is then transected enabling the identification of the junction between the esophagus proximally and the serosa of the stomach distally. Ultimately, the stomach will be divided at the cardiofundic junction, 1 to 2 centimeters below the lower esophageal sphincter.

An incision is then developed through the transverse mesocolon, large enough to accommodate a Roux-en-Y jejunal limb with its associated mesentery (see, e.g., Sapala et al., *Obes. Surg.*, 1998;8:505–516). This window is 3–4 cm in diameter. The Roux-en-Y limb and biliopancreatic limb are measured at 200 and 150 centimeters, respectively (FIG. 1). This leaves a 200 to 400 centimeter common conduit consisting of both distal jejunum and the entire ileum. The proximal jejunum is then divided preferably with a U.S. Surgical Corp. TLC 55 or similar device (e.g., multifire endo GIA, U.S. Surgical Corp.). The mesentery is then immobilized by dividing two vascular arcades, ensuring an adequate limb length from the proximal anastomosis with the micropouch (FIG. 1). The transected ends of the divided small bowel are connected with sutures of lambert 3-0 silk. This is necessary to avoid either a small bowel obstruction or a leak from a staple line itself.

The Roux-en-Y limb of jejunum is then delivered through the opening in transverse mesocolon to lie alongside of the micropouch for the greater curvature gastrojejunostomy.

The proximal stomach is then divided at the cardiofundic junction 1 to 2 centimeters below the cardia junction preferably using a staple gun (ILA 100 mm Stapler, U.S. Surgical Corp.). Care is taken to identify and preserve the nerves along the lesser curvature of the stomach. The proximal limb of jejunum is then attached to the esophagus using a basting suture of 2-0 silk. A second basting suture is used at the apex of the micropouch (FIG. 1).

Gastrotomy and jejunotomy openings are made to accommodate the jaws of a stapler, preferably a GIA 52-mm stapler (U.S. Surgical Corp.) and a retrocolic side to side Roux-en-Y cardiojejunostomy is made along the greater curvature. The anastomosis has an internal diameter of about 10 mm to about 12 mm. The anastomosis is neither reinforced nor banded. The enterostomy (cardiojejunostomy) incisions are closed by approximating the jejunal serosa to the gastric serosa. Since the stoma opening is small, this closure is done using a single layer of lambert silk sutures. The micropouch is now completed with the esophagus proximal to the micropouch. The jejunum lies to its greater curvature side. The bypassed stomach, or a distal gastric remnant, lies inferiorly (FIG. 1). Constructing the micropouch in this manner prevents inclusion of fundal tissue in the micropouch which may result in dilation of the pouch and avoids inclusion of acid producing cells along the lesser curvature which could lead to marginal ulceration. Following closure of the enterotomy incisions, the anastomosis is reinforced with fibrin glue preferably Heemaseel™ (Hemaecure Corp.). The glue polymerizes in 3 to 7 minutes creating a seal along the suture line. The use of fibrin glue in this part of the procedure prevents leaks from the anastomosis which may result in peritonitis. The seal will be absorbed in 5 to 7 days following surgery. The Roux-en-Y jejunum is then anchored to the transverse mesocolon to prevent an internal hernia which can be lethal.

The biliopancreatic conduit is then connected to the common conduit using stapled anastomosis with (preferably) a 2.5-cm lumen (FIG. 1). Specifically, the distal side-to-side jejuno-jejunostomy is made with a GIA 52 stapler. Again, the enterotomy incisions are closed in one layer using 3-0 silk sutures. No fibrin flue is applied over the anastomosis. The small bowel is placed in its normal intracolic position and covered with omentum. The linea alba and skin are closed with staples (Sapala et al., *Surg Gynecol Obstet* 1986; 153: 179–180), and the subcutaneous tissues are drained with a closed Hemovac suction system (Arrow Corp., Norwalk, Conn, USA).

The references cited herein are hereby incorporated by reference in their entirety.

What is claimed is:

1. A surgical method for treating obese patients, the method comprising:

a) incising the patient and entering the abdominal cavity;

b) mobilizing the gastrocolic omentum from the watershed to the angle of His;

c) identifying and transecting the left phrenoesophageal ligament thereby enabling the exposure and identification of the junction of the longitudinal muscle fibers of the esophagus with the serosa of the cardia;

d) opening a window along the lesser curvature of the stomach through the gastrohepatic ligament proximal to the coronary vein;

e) transecting the proximal end of the stomach at the junction of the cardia and the fundus;

f) constructing a micropouch by making a retrocolic side-to-side Roux-en-Y cardiojejunostomy along the greater curvature of the stomach, thereby preventing inclusion of fundal tissue and lesser curvature acid producing cells in the micropouch;

g) incorporating the proximal fundus of the cardia into the stoma of the anastomosis;

h) closing the gastrotomy and jejunotomy incisions without inverting the staple line at the apex of the micropouch;

i) applying fibrin glue over the closure specified in h); and j) connecting the biliopancreatic limb to the common conduit via side-to-side jejuno-jejunostomy.

2. The method of claim 1 wherein the gastrocolic omentum is mobilized using a multifire endo-GIA stapler.

3. The method of claim 1 wherein the stoma of step (g) is approximately 12 mm in diameter.

4. The method of claim 1 wherein the fibrin glue is Heemaseal.

* * * * *